United States Patent
Laske et al.

(12) 
(10) Patent No.: US 7,045,279 B1
(45) Date of Patent: May 16, 2006

(54) ISOLATED PERFUSED HEART PREPARATION AND METHOD OF USE

(75) Inventors: Timothy G. Laske, Shoreview, MN (US); Paul A. Iaizzo, White Bear Lake, MN (US); Mark A. Hjelle, White Bear Lake, MN (US); Josée Morissette, Minneapolis, MN (US); Dale A. Wahlstrom, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/419,271

(22) Filed: Oct. 15, 1999

Related U.S. Application Data

(60) Provisional application No. 60/105,241, filed on Oct. 22, 1998.

(51) Int. Cl.
*C12N 5/00* (2006.01)

(52) U.S. Cl. .................. 435/1.2; 435/1.1; 435/374; 436/18; 600/481

(58) Field of Classification Search ............... 435/1.1, 435/1.2, 374; 436/18; 600/481
See application file for complete search history.

(56) References Cited

U.S. PATENT DOCUMENTS

| | | | |
|---|---|---|---|
| 3,607,646 A | * | 9/1971 | Roissart |
| 5,075,210 A | * | 12/1991 | Wikman-Coffelt |
| 5,716,378 A | * | 2/1998 | Minten |
| 5,807,737 A | * | 9/1998 | Schill et al. |

FOREIGN PATENT DOCUMENTS

| WO | WO 91/14364 | * | 10/1991 |
|---|---|---|---|

OTHER PUBLICATIONS

"Influence of Mitral Valve Prosthesis or Rigid Mitral Ring on Left Ventricular Pump Function" by van Rijk–Zwikker et al, Circulation vol. 80, Sep. 1989, Supplement 1, pp. 1–1–1–7.

"Mitral Valve Anatomy and Morphology: Relevance to Mitral Valve Replacement and Reconstruction" by van Rijk–Zwikker et al, Journal of Cardiac Surgery, 1994; 9 (Suppl) pp. 256–261.

"The Isolated Perfused Heart" by Langendorff et al, Biomesstechnik—Verlag, March GmbH, D–7806 March.

* cited by examiner

*Primary Examiner*—Leon B. Lankford, Jr.
(74) *Attorney, Agent, or Firm*—Girma Wolde-Michael; Michael C. Soldner

(57) ABSTRACT

An isolated heart preparation in which essentially normal pumping activity of all four chambers of the heart is preserved, allowing for the use of the preparation in conjunction with investigations of electrode leads, catheters, cardiac implants and other medical devices intended to be used in or on a beating heart. The preparation may also be employed to investigate heart functions, in the presence or absence of such medical devices. In order to allow for visualization of heart structures and devices located within the chambers of the heart, a clear perfusate such as a modified Krebs buffer solution with oxygenation is circulated through all four chambers of the heart and the coronary vasculature. The preparation and recordings of the preparation may be used in conjunction with the design, development and evaluation of devices for use in or on the heart, as well as for use as an investigational and teaching aid to assist physicians and students in understanding the operation of the heart.

11 Claims, 3 Drawing Sheets

ISOLATED PERFUSED HEART PREPARATION AND METHOD OF USE

This application claims priority from U.S. Provisional Patent Application No. 60/105,241 filed Oct. 22, 1998, incorporated herein by reference in its entirety.

BACKGROUND OF THE INVENTION

Oscar Langendorff is credited with first devising a method to permit investigation of the mechanical activity of the completely isolated mammalian heart. The basic mechanism employed by Langendorff is to force blood or other oxygenated fluid through the coronary vasculature by means of a catheter inserted in the ascending aorta. The oxygen carrying fluid (perfusate) passes through the coronary arteries and coronary veins and exits the coronary sinus, keeping the heart alive. However, during the Langendorff procedure, the ventricular chambers of the heart are essentially empty, and the heart therefore does not beat in a mechanically normal fashion.

In the article "Influence of Mitral Valve Prosthesis or Rigid Mitral Ring on Left Ventricular Pump Function" by van Rijk-Zwikker et al., Circulation Vol. 80, September 1989, Supplement 1, pp. I-1–I-7, a roller pump driven transparent electrolyte circuit including the left atrium and ventricle was added to an isolated heart employing perfusion of the coronary arteries with blood from a support animal. This preparation was employed to study left ventricular function. This same preparation was apparently used to study mitral valve function as describe in the article "Mitral Valve Anatomy and Morphology: Relevance to Mitral Valve Replacement and Reconstruction" by van Rijk-Zwikker et al., Journal of Cardiac Surgery, 1994; 9 (Suppl) pp. 256–261.

SUMMARY OF THE INVENTION

The present invention is directed toward an isolated large mamalian heart preparation in which essentially normal pumping activity of all four chambers of the heart is preserved, allowing for the use of the preparation in conjunction with investigations of electrode leads, catheters, cardiac implants and other medical devices intended to be used in or on a beating heart. The preparation may of course also be employed to investigate heart functions or dysfunctions, in the presence or absence of such medical devices. In order to allow for visualization of heart structures and devices located within the chambers of the heart, a clear perfusate such as a modified Krebs buffer solution with oxygenation is circulated through all four chambers of the heart and the coronary vasculature. Because the preparation does not require separate perfusion of the coronary arteries, the preparation is simpler to produce and more accurate in its simulation of normal heart functioning. The heart employed may be a normally functioning heart or may have a naturally occurring or induced disease or defect.

The isolated heart preparation is produced by first exposing the heart of the donor, animal or human, from which it is to be harvested, followed by introduction of cardioplegic solution into the aorta to arrest the heart. The heart is then excised and cannulated, with cannulas coupled to the aorta, inferior vena cava, pulmonary artery and a pulmonary vein. The superior vena cava is either clamped or fitted with a camera access cannula. The heart is then mounted in a temperature control jacket and coupled to an external oxygenator and associated pumps, which provide oxygenated perfusate to the left atrium, typically via the pulmonary vein and perfusate to the right atrium, typically via the inferior vena cava or superior vena cava. Outflow from the aorta is returned to a cardiotomy reservoir, as is outflow from the pulmonary artery. Fluid columns are associated with the pumps, which deliver perfusate to the inferior vena cava and pulmonary vein and maintain appropriate preload pressures. Oxygen bubblers may optionally be placed in the fluid columns for additional oxygenation of the perfusate.

Optical viewing equipment such as fiber optic scopes can be passed into the preparation through any of the cannulas, allowing for visualization of any of the four chambers, while the heart continues to beat normally. Additionally or alternatively, such viewing equipment may be passed through the wall of a chamber or chambers of the heart to directly access the chamber. Implantable catheters, pacing leads, heart valves and other equipment may also be advanced into or inserted into the heart, and their performance and behavior monitored by means of the optical viewing equipment. The condition and function of previously implanted cardiac prostheses such as heart valves or previously implanted cardiac leads may also be observed. In addition, the preparation may be used to assess the acute functioning of the heart and operation of electrodes, catheters and other devices inserted into the pericardial space or mounted to the surface of the heart or pericardium, which devices may be observed visually.

As part of such investigations or independently, physiologic assessment of cardiac performance can be obtained using available instrumentation to monitor the ECG, heart rate, heart chamber pressures, heart tissue contractility, heart wall motion, gas concentrations and/or fluid flow through the chambers and in the coronary vasculature. Visual imaging of the exterior of the preparation and/or imaging using ultrasound, fluoroscopy, MRI or other medical imaging systems may also be performed. The preparation thus has a wide variety of valuable uses in conjunction with the design, development and evaluation of devices for use in or on the heart, as well as for use as an investigational and teaching aid to assist physicians and students in understanding the operation of the heart.

DETAILED DESCRIPTION OF THE PREFERRED EMBODIMENTS

Figure 1:
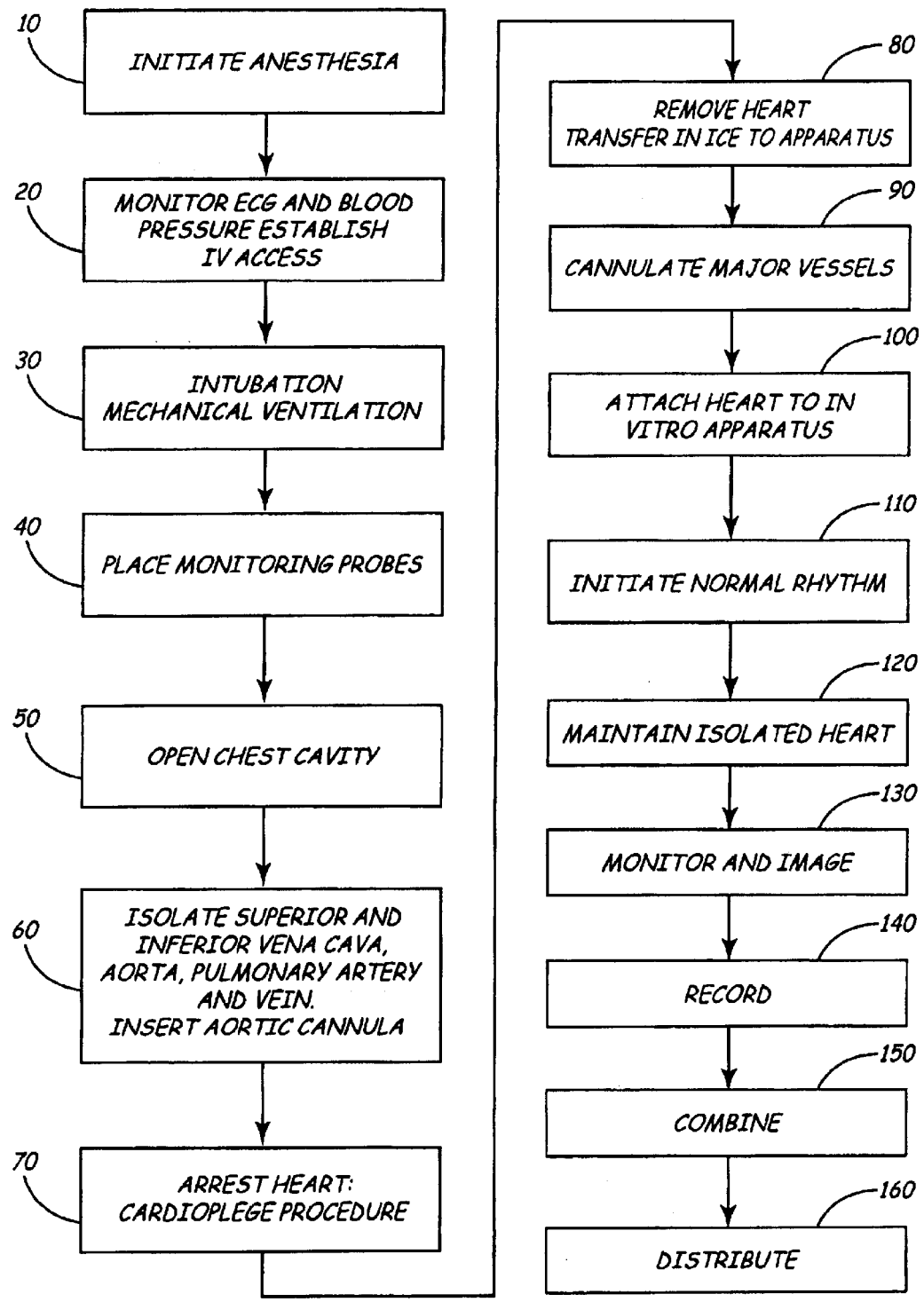
FIG. 1 is an exemplary flow chart illustrating the steps involved in preparing an isolated heart preparation according to the present invention.

FIG. 1 is a flow chart illustrating the various steps involved in producing the isolated heart preparation of the present invention. The exemplary procedure, which follows, has parameters that are appropriate for use in conjunction with an excised swine heart. These parameters would of course need to be adjusted appropriately in conjunction with isolated heart preparations using hearts obtained from human or other animal donors.

The first step, indicated at 10, is the initiation of anesthesia. Assuming that the donor for the heart is, for example, a 30 to 40 kilogram swine, the animal may be anesthetized by intramuscular injection, for example by injection of 150 milligrams of Telezol (Tiletamine HGL and Zolazepam), 150 milligrams Xylazin and 800 micrograms of Atropine. The Telezol and Xylazin render the animal unconscious while the Atropine acts as an anticholinergic, which dries up secretions and stabilizes the heart.

The next step, indicated at 20, is to monitor the blood pressure and the cardiac electrogram of the animal and establish IV access. This is accomplished by positioning the animal and securing it to the operating table, attaching electrocardiac leads to the animal to monitor the ECG and inserting an intravenous line into the animal's ear vein. The intravenous drip may comprise two to three liters of Ringer's solution continuously administered through the operation, containing 20 milligrams per kilogram of Thiopental, a short acting anesthetic. 5-milligram doses of Pancuronium or Vecuronium (or other non-depolarizing muscle relaxants) may also be administered to temporarily paralyze the animal's muscles.

The next step, indicated at 30, is intubation and beginning of mechanical ventilation. This step is accomplished by inserting an endotracheal tube for mechanical ventilation and use of inhalation anesthetics. Any mode of general anesthesia o muscle relaxants may be employed. For example, the administered gas may be approximately 50 percent oxygen and 50 percent nitrous oxide plus an additional 0.8 percent Halothane or an appropriate dosage of any other anesthetic to anesthetize the animal. Exhaled carbon dioxide and Halothane levels are monitored according to standard operating room procedures and the levels of the administered gas components are titrated to maintain normal hemodynamic parameters.

The next step, indicated at 40, is the placement of monitoring probes. This is accomplished using standard operating room pressure measurement probes such as a Swan-Ganz catheter, Millar pressure transducer catheter, etc. for in-vivo blood pressure measurements.

The next step, indicated at 50, is the opening of the chest cavity. This is accomplished by making a longitudinal incision along the midline, cutting the sternum along the midline, and retracting the ribcage to expose the heart and great vessels. A lateral approach may also be employed. The pericardium may then be excised and pericardial fat and other connective tissues removed. Alternatively, the pericardium may be left intact if evaluation of devices employed in the pericardial space is desired.

The next step, indicated at 60, includes the isolation of superior and inferior vena cava, the aorta, the pulmonary artery and pulmonary vein, along with the insertion of the aortic cannula. This is accomplished by dissecting out the major blood vessels listed above for clamp placement and transsection, followed by introduction of an aortic cardioplegic cannula, for example a nine French double lumen cannula. Prior to placement of the aortic cannula, heparin is delivered to prevent coagulation. If desired, adenosine may be introduced to dilate coronary vessels and prepare the heart for cardioplegia. The inferior vena cava is then tied off at one or two spaced locations, the superior vena cava is clamped at one or two spaced locations and the aorta is clamped distally from the insertion site of the aorta cardioplegic cannula.

The next step, indicated at 70, comprises arresting the heart and initiating the cardioplegia procedure. This step is accomplished by initiating antegrade coronary flow of cardioplegia solution through the aortic cannula, for example one to two liters of St. Thomas Hospital cardioplegia solution. Delivery of the cardioplegia solution stops the electrical activity of the heart, due to the high potassium content. Topical cold in the form of ice or a slurry of buffers is applied to the heart to slow any remaining myocardial activity, and the left ventricle is decompressed through a pulmonary artery puncture.

The next step, indicated at 80, comprises the removal of the heart and transfer of the heart in ice to a fluid bath to maintain the heart in a cooled condition. In this step, continuous low flow cardioplegia may be maintained by means of the aortic cannula. The inferior vena cava and superior vena cava are then cut. The aorta is cut as distal to the clamp as possible (e.g. beyond the arc so that a portion of the descending aorta is removed) and the pulmonary vein is excised.

The next step, indicated at 90, is to cannulate the major vessels. This step is accomplished by recannulating the aorta using a larger cannula, for example a 40–50 French cannula secured directly into the aorta. The pulmonary vein is cannulated, for example using a 28–40 French cannula. The right atrium is cannulated, for example with a 36–40 French cannula inserted into the inferior vena cava. The superior vena cava, any viewing equipment passing through the wall of any heart chamber and any other remaining openings are sutured to eliminate leaks of perfusate.

The next step, indicated at 100, is the attachment of the heart to the associated apparatus for oxygenating and delivering the clear perfusate. This step is discussed in more detail in conjunction with the description of the equipment associated with the heart in FIG. 2, below. The associated apparatus includes two perfusion pumps for delivering perfusate to the right and left chambers of the heart, fluid columns to adjust input (pre-load) to the right and left atria to appropriate physiologic pressures and to mimic vascular resistance (after-load), and an optional water bath, in which the heart may be located to control the overall temperature of the preparation.

The next step, indicated at 110, is the reinitiation of normal rhythm. This may be accomplished by placing a epicardial defibrillation electrode on the surface of the left ventricle, cannulating the superior vena cava and passing a defibrillation lead through the cannula, through the right atrium and into the right ventricle and thereafter delivering a defibrillation shock between the two electrodes to initiate normal rhythm. The cannula located in the superior vena cava preferably extends upward a sufficient distance to prevent leakage from the right atrium and may be employed to introduce additional or alternative leads, catheters or viewing equipment into the right atrium or ventricle. The defibrillation lead preferably includes cardiac pacing and sensing electrodes that may be used to moderate and control the heart rhythm as necessary in conjunction with an associated external cardiac pacemaker.

The last step, indicated at 120 is to maintain the isolated heart. This is accomplished by employing the associated equipment to deliver a clear, oxygenated perfusate such as a modified Krebs buffer solution adjusted to physiological conditions of pH and calcium. In addition, epinephrine, milrinone or other ionotrope may be added to the perfusate if the heart is not beating to increase the sensitivity to defibrillation. Lidocaine or other anesthetic may be added to the perfusate as a local anesthetic, reducing likelihood of ventricular arrhythmias. Other pharmacological treatment as appropriate may be administered in order to support the preparation.

Once the preparation is established, it may be employed at 130 to generate information with regard to heart function alone or in conjunction with medical devices inserted in or mounted to the preparation. Monitoring of heart function may comprise the insertion of optical viewing equipment into a chamber or a blood vessel of the preparation and/or imaging the preparation using an external video camera, fluoroscope, infrared camera, chemical imaging system (e.g. Ramon spectroscopy), ultrasound, MRI or other imaging method, and/or monitoring the physiologic performance of the heart, including hemodynamic and electrical functioning of the heart. Equipment for monitoring hemodynamic and electrical heart functions may for example include heart sound monitors such as phonocardiograph equipment or other microphones, electrogram sensors, heart rate sensors, pressure sensors, gas concentration sensors, and/or flow sensors located in the chambers and/or in the coronary vasculature of the preparation. The outputs of the various imaging devices and sensors may be recorded at 140 to provide a record of the monitored parameters alone or in conjunction with one another. The recorded outputs of the optical viewing equipment, imaging devices and/or sensors may be combined at 150 to provide a recording, which will allow for simultaneous display of the obtained images and/or monitored cardiac parameters. The recordings obtained may be duplicated and distributed at 160, in the form of CD ROMs, video tape, electronic files, movies, or the like, allowing for the information obtained using the preparation to be widely available to physicians and students.

Figure 2:
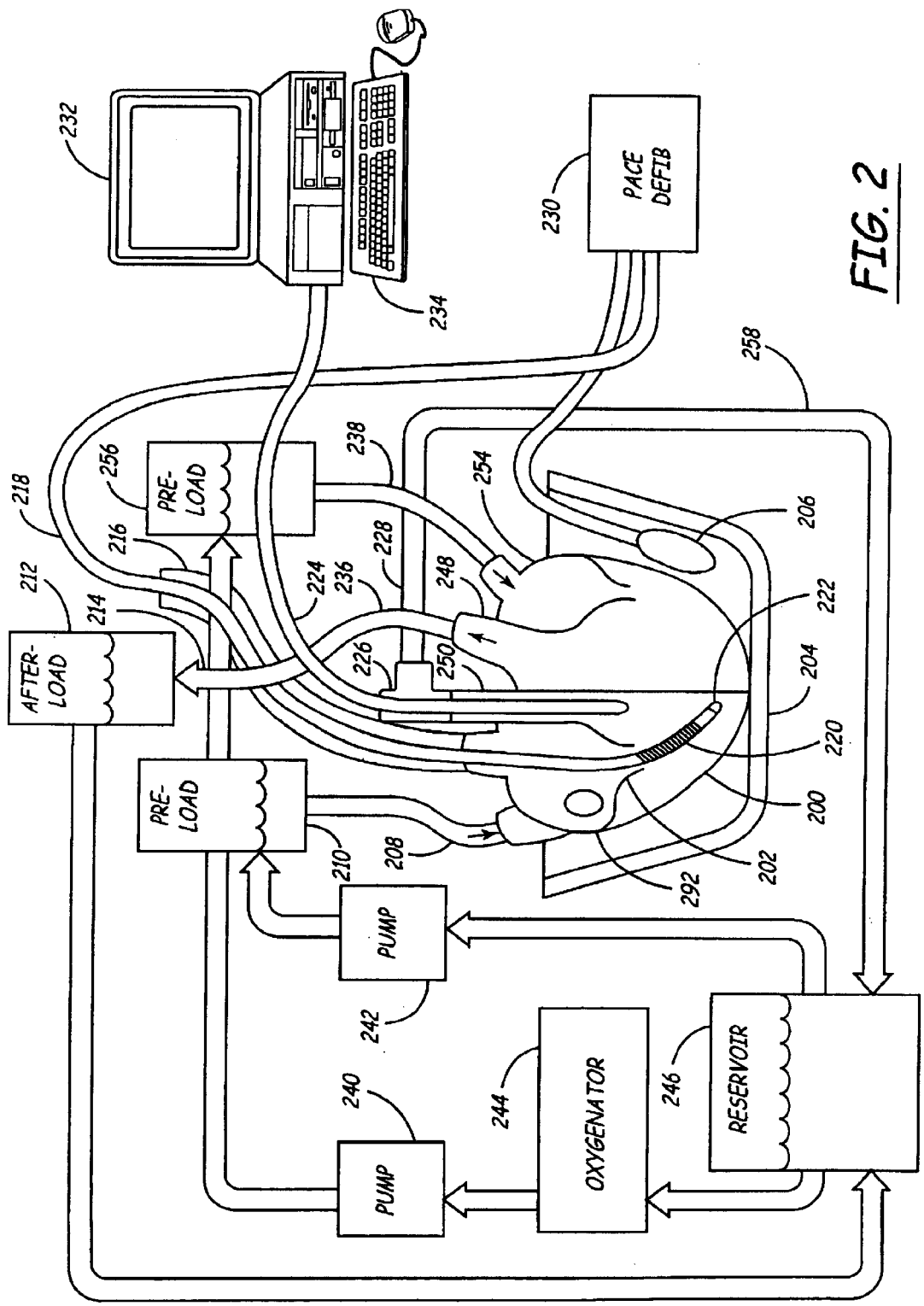
FIG. 2 is a block functional diagram illustrating an exemplary interconnection of the isolated heart preparation according to the present invention and associated support equipment.

FIG. 2 is a schematic diagram of the isolated heart 200 in conjunction with associated equipment employed to maintain the preparation and to evaluate medical devices in conjunction with the preparation. The preparation is maintained in a support apparatus illustrated schematically at 204, which may include a support of surgical netting. The preparation may simply hang suspended in the support netting in a position with the atria located above the ventricles or may be re-oriented to simulate the position of the heart in the donor species in upright, reclining or other positions. The pericardium of the excised hear may also be used as a support, and the heart preparation may be positioned as desired (e.g. vertically or horizontally) to mimic a desired physiological condition. The preparation is maintained at physiological temperature, either by means of the perfusate in combination with the surrounding ambient temperature or optionally by means of an optional temperature control bath. An oxygenator 244 with associated cardiotomy reservoir 246 is coupled to the preparation such that the drain from the pulmonary artery 250 and the output of the aorta 248 both feed the cardiotomy reservoir 246 associated with the oxygenator 244. The right atrium chamber filling pump 242 draws perfusate from the reservoir directly and delivers it to the right atrial preload chamber 210 which comprises a fluid column adjusted to maintain approximately 5 mm Hg pressure going into the right atrium 252 via cannula 208 coupled to the inferior vena cava. The outlet of the pulmonary artery 250, as noted above, drains into the reservoir 246 to complete the circulation path for the right side of the heart. Return flow of perfusate from the coronary sinus is allowed to enter the right atrium or can be separately cannulated to allow periodic sampling or monitoring of the perfusate.

A second pump 240 pumps perfusate from the reservoir 246, through the oxygenator 244 and to the left atrium 254 by means of the cannula 238 inserted into the pulmonary vein. A left atrium preload chamber 256 comprises a fluid column that maintains approximately a 10 mm Hg input pressure into the left atrium. The outflow from the aorta 248 is delivered via cannula 236 to the reservoir 246, against an aortic afterload chamber 212 which defines a fluid column which maintains an average pressure of approximately 70 mm Hg, opposing outflow of fluid from the aorta and mimicking vascular flow impedance. Perfusate enters the coronary arteries from the aortic root, providing for oxygenation of the heart tissue without separate cannulation of the coronary arteries. A port may optionally also be installed in the aortic cannula to allow periodic sampling or monitoring of the perfusate. Either or both of the preload chambers may be fitted with oxygen bubblers to increase oxygenation of the perfusate if desired.

The apparatus described above in conjunction with the preparation may, if desired, be powered by means of storage batteries and mounted in a wheeled cabinet, allowing the preparation to be readily moved from one location to another. The preparation so configured may be employed as a teaching aid in multiple classrooms and/or may be conveniently moved between different laboratories or research facilities.

Also illustrated in conjunction with the preparation is an optical viewing scope 224, for example a fiber optic viewing scope 224 and associated display 232 and control keyboard 234. Scope 224 is inserted into one or more of the chambers of the heart, for example by means of a T-fitting 226 associated with one of the four cannulas coupled to the heart. In the drawing as illustrated, the T-fitting is associated with the cannula 258 coupled to the pulmonary artery 250, allowing for visualization of the right chambers of the heart. However, the optical scope may as well be inserted into the left side of the heart, for example, via the aorta or pulmonary vein.

Alternately, the viewing scope 224 may be passed through the wall of a chamber of the heart, for example through the right atrial appendage and secured by means of a purse-string suture to minimize leakage.

With the optical scope in place allowing observation of a desired chamber of the heart, a medical device intended for use in the heart may be inserted therein. For example, a cardiac pacing lead, cardiac ablation catheter, diagnostic catheter, or other medical device, may be inserted into the heart, and monitored under visual observation using the optical scope, for example by being passed through the cannula 216 coupled to the superior vena cava in the same manner as the pacing/defibrillation lead 220 as illustrated. Additionally, surgical implants such as cardiac valves and atrial septal defect devices may also be tested in conjunction with the isolated heart preparation, under observation of the fiber optic scope. For example, a prosthetic device such as a tricuspid valve may be implanted into the test animal in place of the natural valve 202, weeks, days or months prior to harvesting the animal's heart. Using the isolated heart preparation, the condition and operation of the prosthetic devices may be monitored optically, while the heart beats in an essentially normal fashion.

Figure 3:
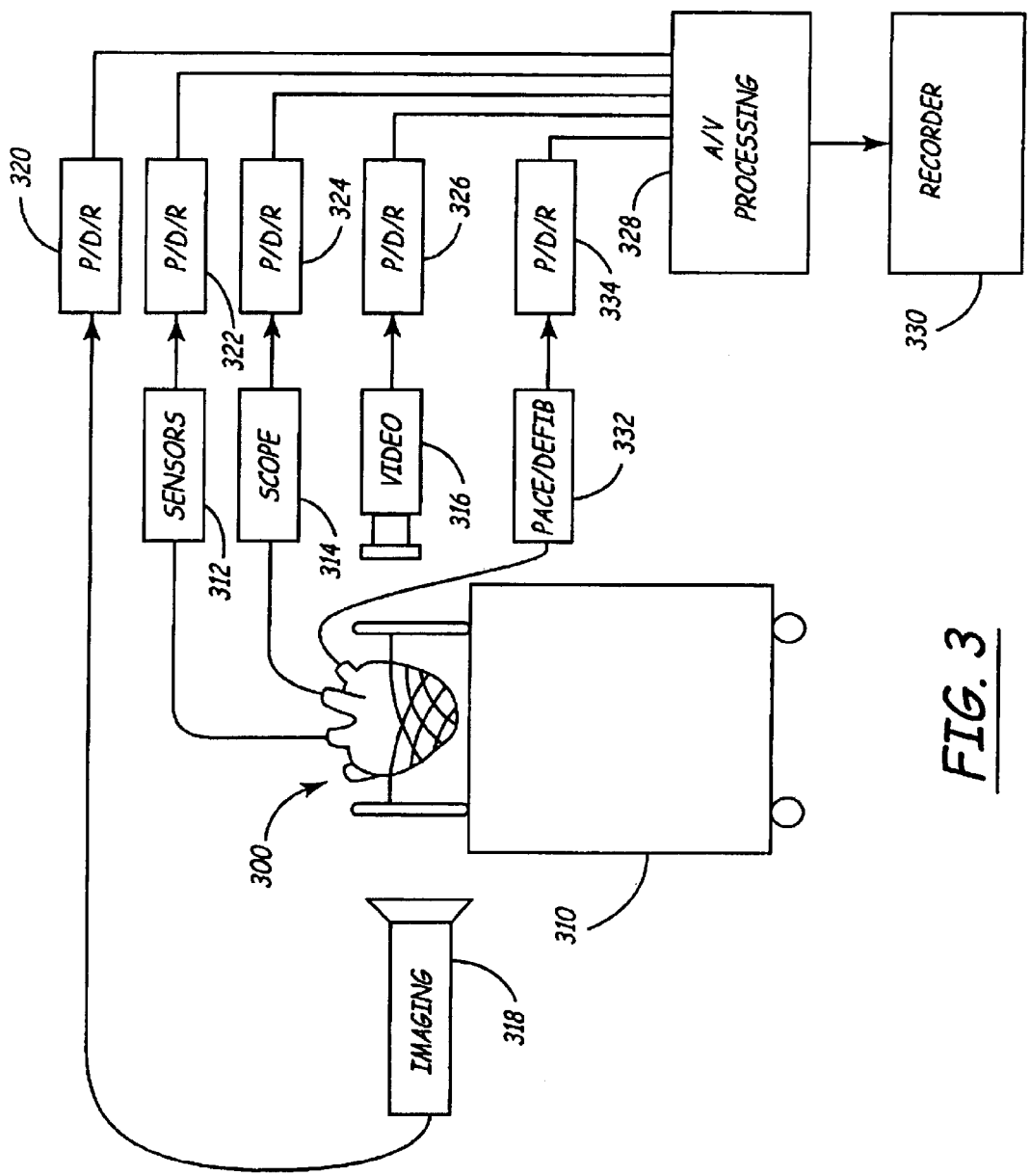
FIG. 3 is a functional diagram illustrating the preparation of the isolated heart preparation according to the present invention in conjunction with monitoring and imaging equipment.

FIG. 3 illustrates schematically the preparation of the present invention in conjunction with imaging and monitoring equipment and audiovisual processing equipment appropriate for producing recordings combining the outputs of the imaging and monitoring equipment. The preparation is illustrated at 300, shown suspended over a cabinet 310 that contains or supports the apparatus illustrated in FIG. 2, with the possible exception of the display 232 and associated control keyboard 234. Interconnection of the chambers of the heart with the equipment illustrated in FIG. 2 is omitted for the sake of simplicity, but corresponds to that illustrated in FIG. 2.

Illustrated schematically in conjunction with the preparation 300 are examples of the types of available monitoring and imaging equipment that may be used in conjunction with the preparation. For example, a fiber optic viewing scope 314 may be inserted into one or more chambers of the heart, along with monitors 312 of hemodynamic or electrical hear functions, as discussed above which may be inserted into a chamber of the heart, within the vasculature of the heart, or applied to the exterior surface of the heart. In addition, video imaging by means of a camera 316 of the exterior of the heart may be employed. In addition or alternatively, an imaging apparatus 318 such as a fluoroscope (X-ray), ultrasound scanner, MRI, or other medical imaging system may also be employed.

The obtained images and/or signals obtained from the imaging devices and/or monitoring equipment are preferably all provided to processing, display and recording equipment 320, 322, 324 and 326 of the types typically employed with the imaging and monitoring equipment. The recorded images and/or signals may be combined with one another by means of audio-visual processing equipment 328 and provided to a recorder 330 to produce a combined recording allowing for simultaneous observation of visual imaging and/or recorded monitored parameters and/or other types of medical imaging on a single audio-visual recording. The recording may be reproduced and distributed, for example in the form of CD ROMs, video tapes, movies or electronic files, to allow the information obtained from the preparation to be viewed by physicians and/or students at remote locations.

Also illustrated at 332 is a pacemaker/defibrillator, coupled to the preparation by means of one or more implantable leads. The operation of the pacemaker/defibrillator or other electronic medical device associated with the heart may also be processed, displayed and recorded by means of associated equipment 334 and provided to audio-visual processing equipment 328. In some cases, particularly in those cases in which the operation of a medical device such as a pacemaker or a defibrillator is of interest with regard to the obtained images and/or other monitored parameters, information with regard to the operation of the medical device may also be combined with obtained images and/or other monitored parameters for display and reproduction. For example, in the context of an implantable pacemaker or cardioverter, the device may provide a signal indicative of the electrogram of the heart and may also provide signals indicative of the operation of the device, including sensing of spontaneous depolarizations by the device, delivery of stimulation pulses to the heart, and information regarding other operational parameters of the device. This information may also be displayed in a combined recording, along with simultaneously obtained images and/or monitored parameters.

The preparation may also serve as a mechanism for allowing physicians to practice implant techniques while directly observing the operation of the heart and implanted devices in a beating heart model. In this context, the physician would implant the prosthesis or device, as if in an intact animal, and have the opportunity to observe the progress of the device through the heart and its interaction with the various structures of the beating heart, for example by using a display associated with an optical probe.

In conjunction with the above specification, we claim:

1. An isolated heart preparation comprising:
   an excised heart including corresponding coronary arteries and veins;
   means for delivering a transparent perfusate through all four chambers of the heart via a cannulated attached aorta, inferior vena cava, pulmonary artery and pulmonary vein; wherein the perfusate flows through the coronary arteries and veins of the heart and oxygenates the heart.

2. The preparation of claim 1 further comprising an optical viewing instrument inserted into a chamber of the heart.

3. The preparation of claim 1 or claim 2 further comprising a medical device applied to the heart.

4. The preparation of claim 3 wherein the medical device is implanted within the heart to monitor and control heart rhythm corresponding to the flow of perfusate.

5. The preparation of claim 1 or claim 2 further comprising a physiologic parameter monitor coupled to the heart.

6. The preparation of claim 1 or claim 2 wherein the delivering means comprises means for delivering the perfusate to right and left atria of the heart.

7. The preparation of claim 6 wherein the means for delivering said perfusate to right and left atria of the heart comprises means for providing pre-load pressure.

8. The preparation of claim 7 wherein the means for providing pre-load pressure comprises a fluid column.

9. The preparation of claim 1 or claim 2 wherein the delivering means comprises means for receiving the perfusate from right and left ventricles of the heart.

10. The preparation of claim 9 wherein the receiving means comprises means for mimicking vascular impedance.

11. The preparation of claim 10 wherein the means for mimicking vascular impedance comprises a fluid column.

* * * * *